US009440362B2

(12) United States Patent
Wang

(10) Patent No.: US 9,440,362 B2
(45) Date of Patent: Sep. 13, 2016

(54) ROBOTIC ARM WITH SPHERICAL LINKAGE

(71) Applicant: Hiwin Technologies Corp., Taichung (TW)

(72) Inventor: Ren-Jeng Wang, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 206 days.

(21) Appl. No.: 14/257,597

(22) Filed: Apr. 21, 2014

(65) Prior Publication Data

US 2015/0202780 A1 Jul. 23, 2015

(30) Foreign Application Priority Data

Jan. 22, 2014 (TW) .............................. 103102343 A

(51) Int. Cl.
| | |
|---|---|
| *G05G 11/00* | (2006.01) |
| *B25J 18/00* | (2006.01) |
| *B25J 17/00* | (2006.01) |
| *B25J 9/10* | (2006.01) |

(52) U.S. Cl.
CPC .............. *B25J 18/005* (2013.01); *A61B 34/30* (2016.02); *B25J 9/1045* (2013.01); *B25J 17/00* (2013.01); *A61B 34/71* (2016.02); *Y10S 901/21* (2013.01); *Y10T 74/20329* (2015.01)

(58) Field of Classification Search
CPC ...... B25J 18/005; B25J 18/007; B25J 9/104; B25J 9/1045; B25J 17/00; B25J 17/0258
See application file for complete search history.

(56) References Cited

U.S. PATENT DOCUMENTS

| | | | | |
|---|---|---|---|---|
| 4,717,309 | A * | 1/1988 | Neuhaus ................. | B25J 9/104 269/61 |
| 5,046,375 | A * | 9/1991 | Salisbury, Jr. ........... | B25J 9/046 414/7 |
| 2006/0243085 | A1* | 11/2006 | Hannaford ............. | A61B 19/22 74/490.01 |
| 2007/0089557 | A1* | 4/2007 | Solomon ............ | A61B 19/2203 74/490.01 |
| 2011/0146440 | A1* | 6/2011 | Feng ...................... | B25J 18/007 74/490.1 |
| 2014/0378994 | A1* | 12/2014 | Wang ................. | A61B 19/2203 606/130 |

* cited by examiner

*Primary Examiner* — William Kelleher
*Assistant Examiner* — Zakaria Elahmadi
(74) *Attorney, Agent, or Firm* — Muncy, Geissler, Olds & Lowe, P.C.

(57) ABSTRACT

A robotic arm includes first and second bent links and a tool link pivotally connected in order, first to third wheels, and first to fourth imaginary axes intersecting at a center of spherical rotation. The first bent link and wheel are driven to rotate about the first and third imaginary axes respectively. A first flexible rope is wound around the first and second wheels and fixed to the second bent link for driving the second wheel and bent link to rotate about the second imaginary axis when the first wheel rotates. A second flexible rope is wound around the second and third wheels and fixed to the first bent link for driving the third wheel and the tool link to rotate about the fourth imaginary axis when the second wheel rotates. The robotic arm is relatively smaller, obstructs the operator less and produces a wider sphere of action.

5 Claims, 5 Drawing Sheets

ROBOTIC ARM WITH SPHERICAL LINKAGE

BACKGROUND OF THE INVENTION

1. Field of the Invention

The present invention relates generally to robotic arms and more particularly, to a robotic arm with a spherical linkage.

2. Description of the Related Art

A conventional robotic arm with a spherical five-bar linkage, such as that disclosed in unpublished Taiwan Patent Application No. 102121198, comprises four bent links connected two by two. Each of the bent links is defined with two axes of rotation at two ends thereof, and the axes of rotation all pass through a center of spherical rotation. The robotic arm is primarily applied in a minimally invasive surgery system for installation of a miniature surgical tool and accurate control of swinging direction and angel of the miniature surgical tool.

However, the aforesaid robotic arm is quite large because of having at least four bent links, and the minimally invasive surgery system usually comprises a plurality of robotic arms for installation of a plurality of miniature surgical tools having different functions. Therefore, it would be better to minimize the size of each robotic arm for the convenience of arranging the minimally invasive surgery system in quite limited room for surgery and the minimization of obstructing the motions of medical personnel.

Besides, the movements of the bent links of the aforesaid robotic arm are affected by each other, and drives for driving the bent links to rotate occupy some space around the bent links so as to restrict the rotating angel of each bent link. Therefore, the robotic arm can only drive the miniature surgical tool to move in a quite limited sphere of action.

SUMMARY OF THE INVENTION

The present invention has been accomplished in view of the above-noted circumstances. It is an objective of the present invention to provide a robotic arm with a spherical linkage, which is relatively smaller, therefore obstructs the motions of the operator relatively less and produces a relatively wider sphere of action.

To attain the above objective, the present invention provides a robotic arm which comprises first and second bent links, first and second driving units, first, second and third wheels, first and second flexible ropes, and a tool link. The first bent link has first and second pivoting portions at two ends thereof respectively and is defined with first and second imaginary axes passing through the first and second pivoting portions respectively and intersecting at a center of spherical rotation. The first bent link is driven by the first driving unit to rotate about the first imaginary axis. The first wheel is defined with a third imaginary axis passing through the center of spherical rotation and driven by the second driving unit to rotate about the third imaginary axis. The second bent link has third and fourth pivoting portions at two ends thereof respectively and is defined with a fourth imaginary axis passing through the fourth pivoting portion and the center of spherical rotation. The third pivoting portion of the second bent link is pivotally connected with the second pivoting portion of the first bent link. The second wheel is fixed to the third pivoting portion of the second bent link and pivotally connected with the second pivoting portion of the first bent link. The first flexible rope is wound around the first and second wheels and fixed to the second bent link for driving the second wheel and the second bent link to rotate about the second imaginary axis when the first wheel rotates. The tool link and the third wheel are fixed to each other and pivotally connected with the fourth pivoting portion of the second bent link. The second flexible rope is wound around the second and third wheels and fixed to the first bent link for driving the third wheel and the tool link to rotate about the fourth imaginary axis when the second wheel rotates.

As a result, the robotic arm can be defined with a spherical linkage and adapted for a tool to be installed on the tool link and controlled accurately to swing about the center of spherical rotation. Besides, compared with the conventional robotic arm in a condition of the same function, the robotic arm of the present invention has fewer bent links, therefore is smaller-sized and spares more room for motions of an operator and rotation of each bent link. Therefore, the robotic arm of the present invention obstructs the motions of the operator relatively less and drives the tool to move in a relatively wider sphere of action.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
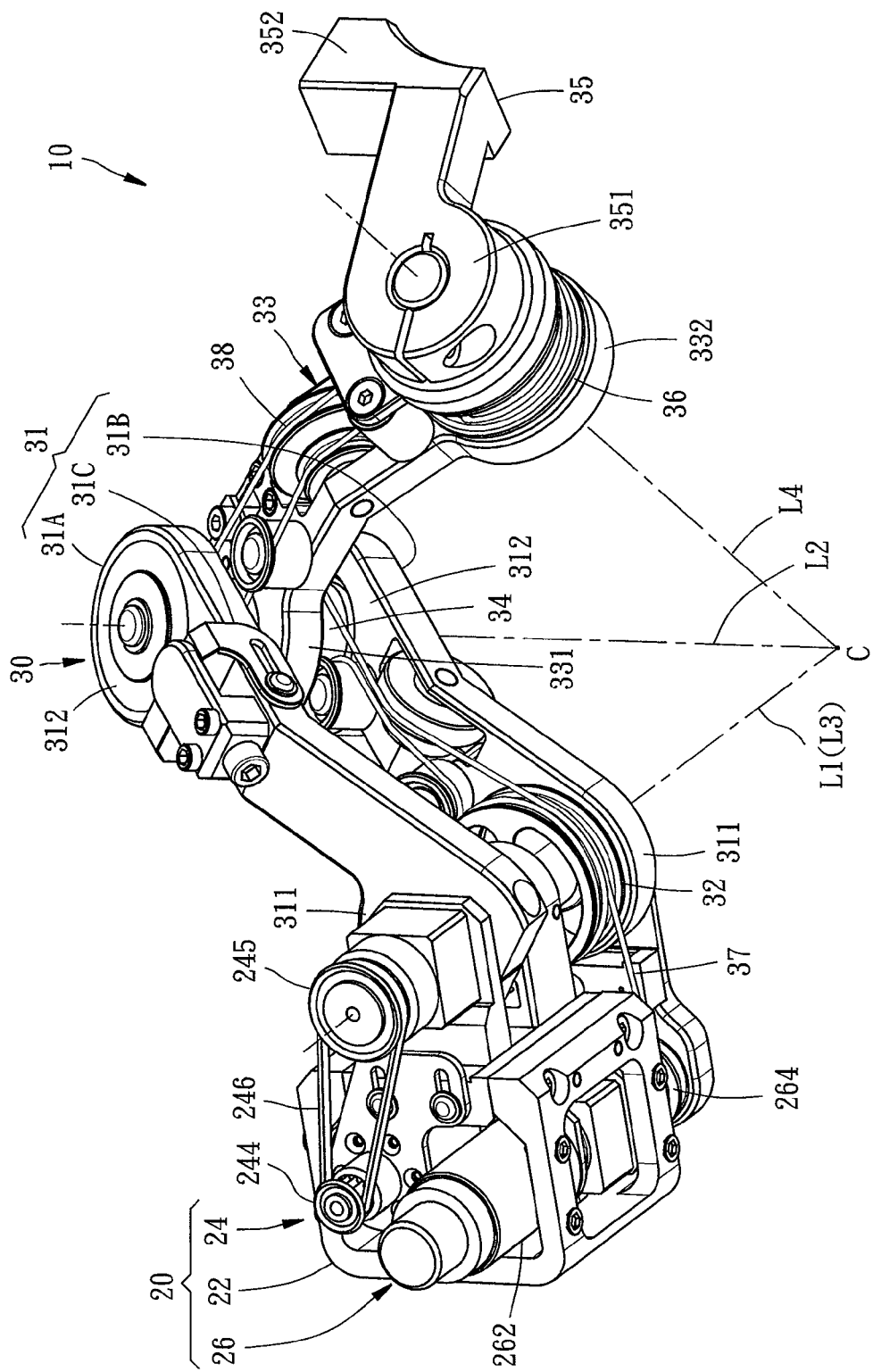
FIGS. 1-3 are perspective views of a robotic arm with a spherical linkage according to a preferred embodiment of the present invention in three different directions.
Figure 2:
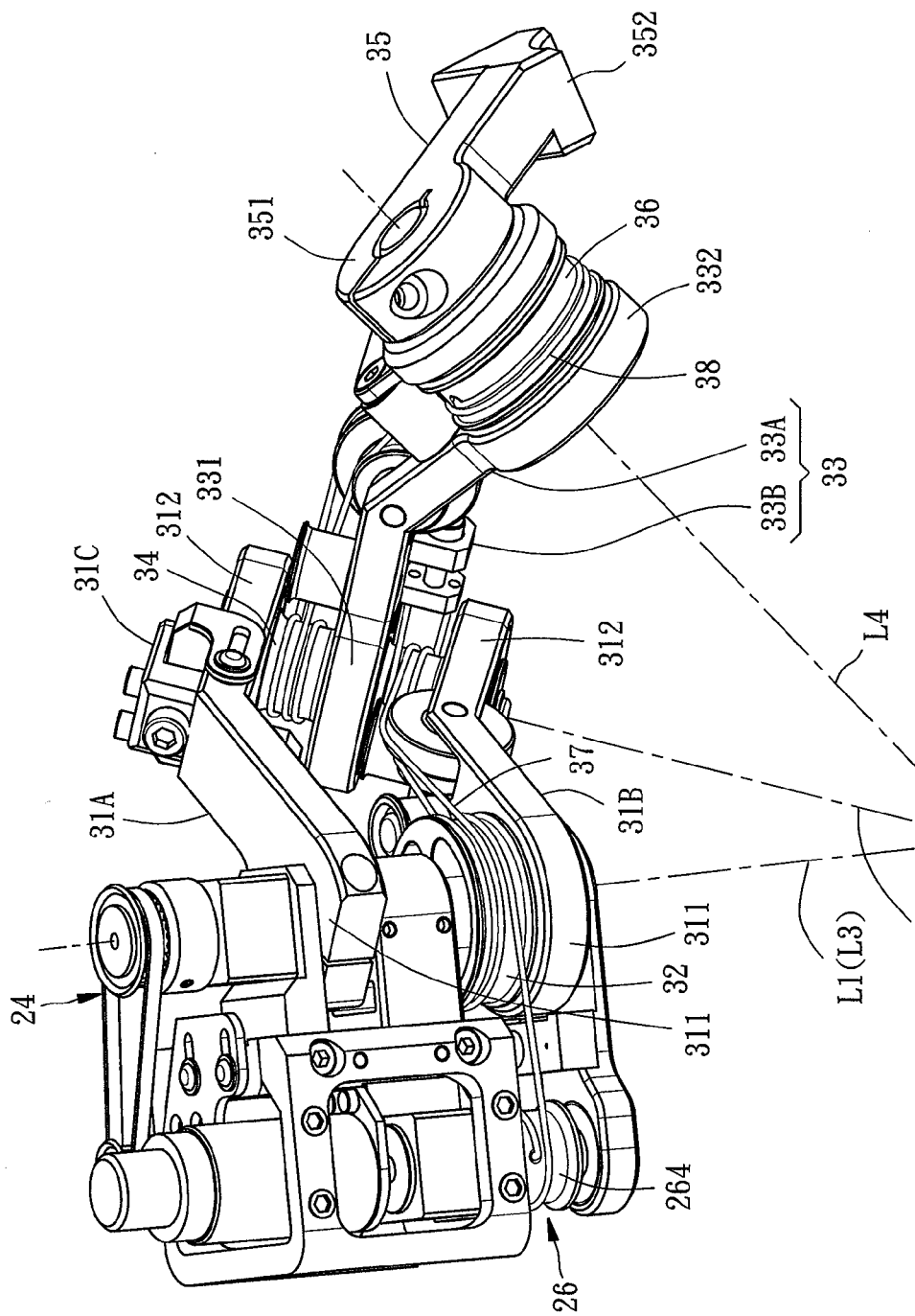
Figure 3:
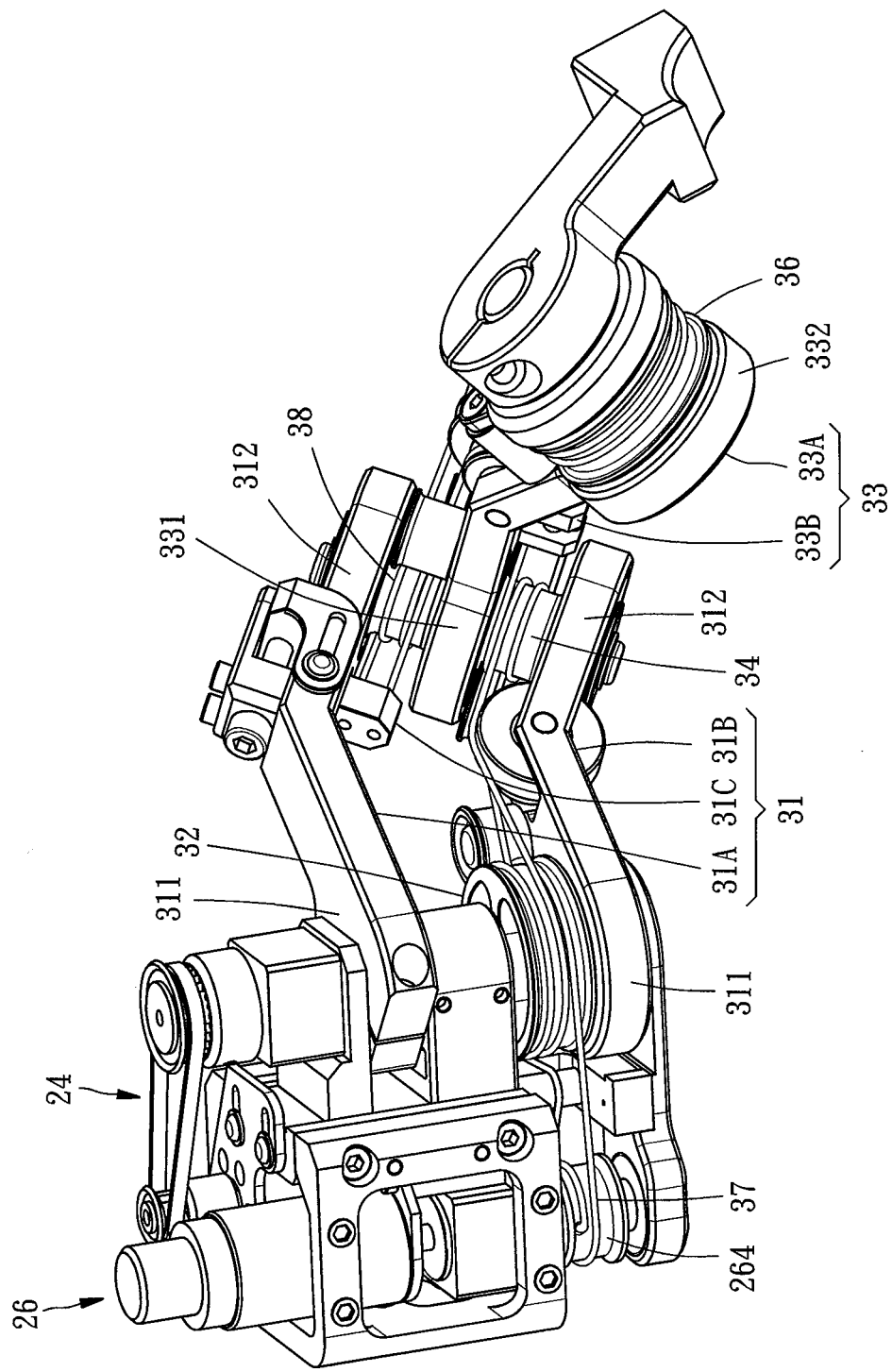
Figure 4:
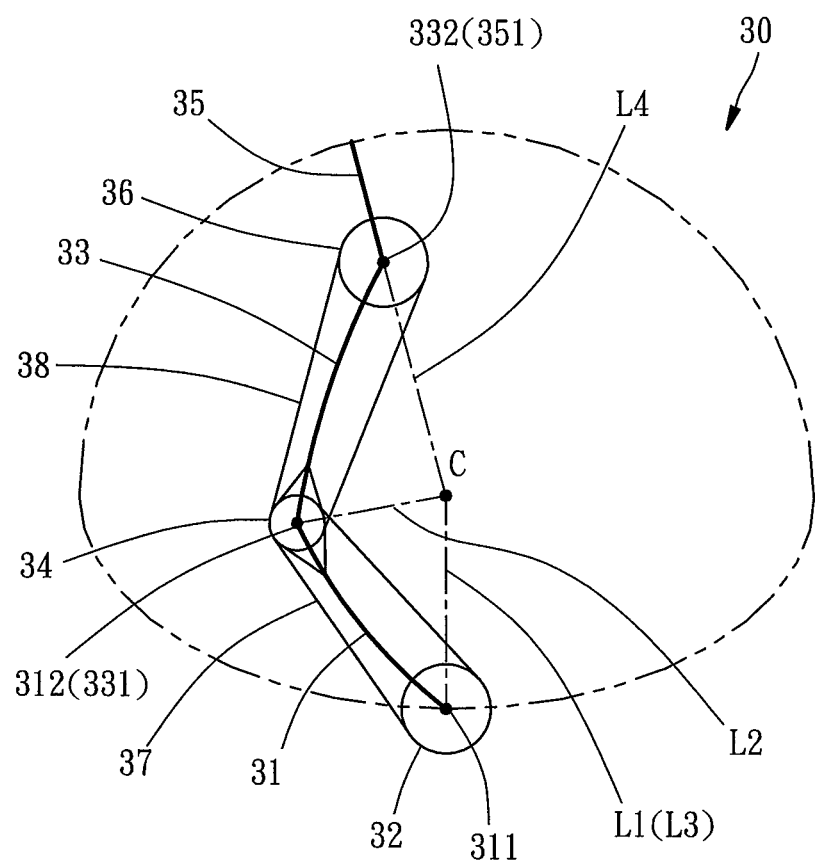
FIG. 4 is a tridimensional schematic drawing of the spherical linkage of the robotic arm according to the preferred embodiment of the present invention.

First of all, it is to be mentioned that same reference numerals used in the following preferred embodiments and the appendix drawings designate same or similar elements throughout the specification for the purpose of concise illustration of the present invention. Besides, when it is mentioned that an element is disposed in/on or connected with another element, it means that the former element is directly connected with the latter element, or the former element is indirectly connected with the latter element through one or more other elements between aforesaid former and latter elements.

Referring to FIGS. 1-4, a robotic arm 10 according to a preferred embodiment of the present invention comprises a driving device 20 and a spherical linkage 30.

It is to be mentioned that the so-called spherical linkage in the present invention is defined with a center of spherical rotation C where the axes of rotation, i.e. first to fourth imaginary axes L1~L4 mentioned in the following paragraphs, of all rotatable portions of the spherical linkage intersect each other. Therefore, when the spherical linkage works, each rotatable portion thereof is considered as moving on an imaginary spherical surface centred around the center of spherical rotation C.

The robotic arm 10 is adapted for a tool device (not shown) to be installed on the spherical linkage 30. The tool device comprises a tool having a specific function, and the tool, such as a miniature surgical tool, is usually disposed to point towards or pass through the center of spherical rotation C approximately. The tool device is driven by the spherical linkage 30 so that the tool substantially swings about the center of spherical rotation C and the swinging direction and angel of the tool is controlled accurately. The configuration of the robotic arm 10 will be specified in the following paragraphs.

The driving device 20 comprises a static base 22, and first and second driving units 24, 26 disposed in the static base 22. The first driving unit 24 comprises a motor (not shown), two pulleys 244, 245 and a belt 246 for transmitting rotary kinetic energy outputted by the motor to the spherical linkage 30. The second driving unit 26 comprises a motor 262 and a transmitting wheel 264 for transmitting rotary kinetic energy outputted by the motor 262 to the spherical linkage 30.

The spherical linkage 30 comprises a first bent link 31, a first wheel 32, a second bent link 33, a second wheel 34, a tool link 35, a third wheel 36, a first flexible rope 37, and a second flexible rope 38.

The first bent link 31 has two bars 31A, 31B moving synchronously, and a tension adjuster 31C disposed on the bar 31A. Each bar 31A, 31B has first and second pivoting portions 311, 312 at two ends thereof respectively. The first bent link 31 is defined with a first imaginary axis L1 passing through the first pivoting portions 311, and a second imaginary axis L2 passing through the second pivoting portions 312. The first and second imaginary axes L1, L2 intersect at the center of spherical rotation C. The first pivoting portions 311 are connected with the pulley 245 of the first driving unit 24 coaxially and driven by the pulley 245 to rotate so that the first bent link 31 is driven by the first driving unit 24 to rotate about the first imaginary axis L1.

Figure 5:
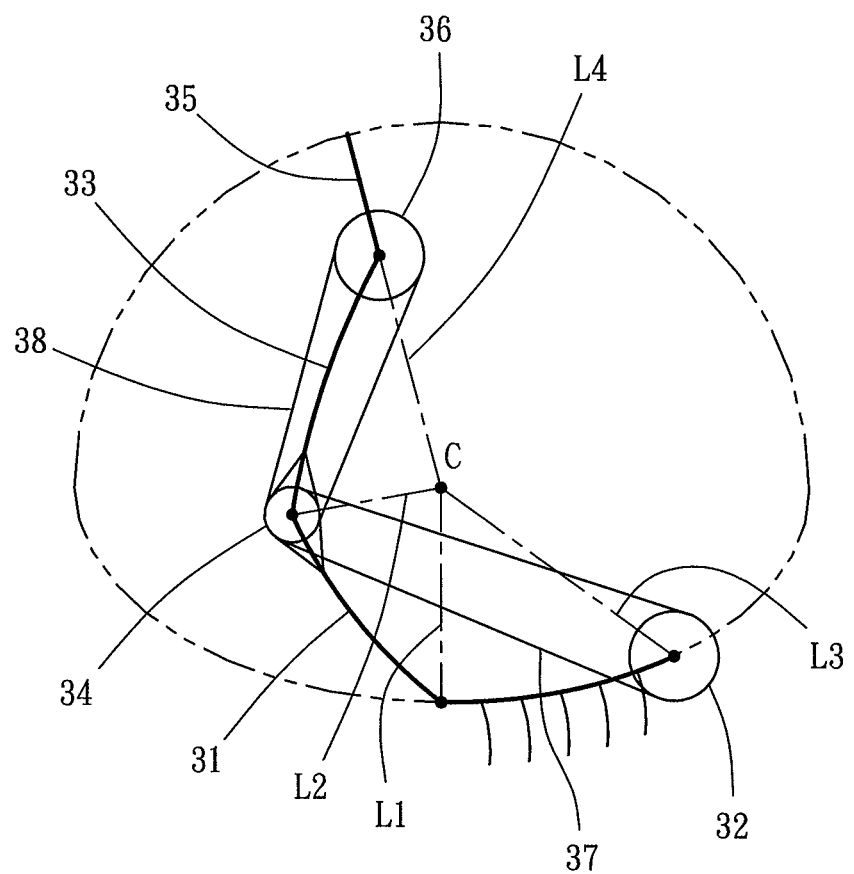
FIG. 5 is similar to FIG. 4 except that first and third imaginary axes of the spherical linkage coincide in FIG. 4 but don't coincide in FIG. 5.

The first wheel 32 is defined with a third imaginary axis L3 passing through the center of spherical rotation C and disposed between the bars 31A, 31B of the first bent link 31. In this embodiment, the first wheel 32 is connected with the first pivoting portion 311 of the first bent link 31 coaxially; therefore, the third imaginary axis L3 coincides with the first imaginary axis L1. However, the first wheel 32 and the first pivoting portion 311 of the first bent link 31 can be disposed not coaxially so that the third imaginary axis L3 doesn't coincide with the first imaginary axis L1, as shown in FIG. 5.

The second bent link 33 has a bar 33A disposed between the bars 31A, 31B of the first bent link 31, and a tension adjuster 33B disposed on the bar 33A. The bar 33A has third and fourth pivoting portions 331, 332 at two ends thereof respectively. The third pivoting portion 331 is pivotally connected with the second pivoting portions 312 of the first bent link 31 and rotatable relative to the second pivoting portions 312 about the second imaginary axis L2. Besides, the second bent link 33 is defined with a fourth imaginary axis L4 passing through the fourth pivoting portion 332 and the center of spherical rotation C.

The second wheel 34 is disposed between the bars 31A, 31B of the first bent link 31 and penetrates the third pivoting portion 331 of the second bent link 33. The second wheel 34 is pivotally connected with the second pivoting portions 312 of the first bent link 31 and fixed to the third pivoting portion 331 of the second bent link 33 so as to rotate with the third pivoting portion 331 synchronously.

The tool link 35 has a fifth pivoting portion 351 and an installation portion 352 at two ends thereof respectively. The fifth pivoting portion 351 is pivotally connected with the fourth pivoting portion 332 of the second bent link 33 and rotatable relative to the fourth pivoting portion 332 about the fourth imaginary axis L4. The installation portion 352 is adapted to be connected with the tool device.

The third wheel 36 is pivotally connected with the fourth pivoting portion 332 of the second bent link 33 and disposed between the fourth pivoting portion 332 and the fifth pivoting portion 351 of the tool link 35. Besides, the third wheel 36 is fixed to the fifth pivoting portion 351 so as to rotate with the fifth pivoting portion 351 synchronously.

Each flexible rope 37, 38 can be, but not limited to, a steel rope. The first flexible rope 37 is wound around the transmitting wheel 264 of the second driving unit 26 and the first and second wheels 32, 34 and fixed to the tension adjuster 33B of the second bent link 33. The second flexible rope 38 is wound around the second and third wheels 34, 36 and fixed to the tension adjuster 31C of the first bent link 31. When the transmitting wheel 264 is driven by the motor 262 to rotate, the first wheel 32 is driven to rotate through the first flexible rope 37 and drives the second wheel 34 and the second bent link 33 to rotate about the second imaginary axis L2. At the same time, the second flexible rope 38 is driven by the second wheel 34 to rotate and drive the third wheel 36 and the tool link 35 to rotate about the fourth imaginary axis L4. Besides, the ratio of the rotating angles of the wheels 32, 34, 36 corresponds to the ratio of the outer radiuses of the wheels 32, 34, 36. Therefore, the second driving unit 26 can control the rotating angles of the second bent link 33 and the tool link 35 by controlling the rotating angel of the first wheel 32.

It will be appreciated that the tension adjuster 31C is adapted for a user to adjust the tension of the second flexible rope 38, and the tension adjuster 33B is adapted for the user to adjust the tension of the first flexible rope 37. However, the first and second bent links 31, 33 can also have no such tension adjusters 31C, 33B, and the flexible ropes 37, 38 are fixed to the bars 33A, 31A, respectively.

In this embodiment, the first and second bent links 31, 33 are substantially equal in length. Besides, the outer radius of the first wheel 32 equals that of the third wheel 36 and doubles that of the second wheel 34; in other words, the ratio of the outer radiuses of the first to third wheels 32, 34, 36 is 2:1:2. In this way, no matter how the tool link 35 works, the fifth pivoting portion 351 will approximately point towards the first pivoting portion 311 of the first bent link 31 so that the installation portion 352 will point opposite to the first pivoting portion 311. This feature can prevent the tool device from bumping against the spherical linkage 30 or the driving device 20 and simplify the calculation of the program for controlling the spherical linkage 30. However, the robotic arm of the present invention is not limited to have this feature.

As regards the words mentioned in the present invention that the first and second bent links are substantially equal in length, the length of the first bent link 31 is defined as the distance between the first and second imaginary axes L1, L2 on an imaginary spherical surface where the first and second pivoting portions 311, 312 of the bar 31A or 31B are located. In other words, the length of the first bent link 31 is defined as the length of an imaginary arc which is located on the aforesaid imaginary spherical surface defined by the first and second pivoting portions 311, 312 and has two ends at the centers of the first and second pivoting portions 311, 312. By the same definition, the length of the second bent link 33 is defined as the distance between the second and fourth imaginary axes L2, L4 on an imaginary spherical surface where the third and fourth pivoting portions 331, 332 are located. In other words, the length of the second bent link 33 is defined as the length of an imaginary arc which is located on the aforesaid imaginary spherical surface defined by the third and fourth pivoting portions 331, 332 and has two ends at the centers of the third and fourth pivoting portions 331, 332. Besides, the outer radiuses of the first to third wheels 32, 34, 36 mentioned in the present invention are respectively defined as the radiuses of curvature of the wheels' cylindrical surfaces where the flexible ropes 37, 38 are wound.

Compared with the conventional robotic arm mentioned in the description of the related art, the robotic arm 10 of the present invention has not only the same function but also advantages of fewer bent links and thereby a smaller size. Therefore, when applied in a minimally invasive surgery system, the robotic arm 10 of the present invention is easier to be arranged in quite limited room for surgery than the conventional robotic arm and spares relatively more room for motions of the operator even to the extent that left-handed and right-handed operators can both act swimmingly. Besides, the rotating angel of each bent link is relatively less confined because the robotic arm 10 has relatively fewer bent links so that the tool device can be driven to move in a relatively wider sphere of action.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A robotic arm comprising:
    a first bent link having first and second pivoting portions at two ends thereof respectively and defined with first and second axes passing through the first and second pivoting portions respectively and intersecting at a center of spherical rotation;
    a first driving unit for driving the first bent link to rotate about the first axis;
    a first wheel defined with a third axis passing through the center of spherical rotation;
    a second driving unit for driving the first wheel to rotate about the third axis;
    a second bent link having third and fourth pivoting portions at two ends thereof respectively and defined with a fourth axis passing through the fourth pivoting portion and the center of spherical rotation, the third pivoting portion of the second bent link being pivotally connected with the second pivoting portion of the first bent link;
    a second wheel fixed to the third pivoting portion of the second bent link and pivotally connected with the second pivoting portion of the first bent link;
    a first flexible rope wound around the first and second wheels and fixed to the second bent link for driving the second wheel and the second bent link to rotate about the second axis when the first wheel rotates;
    a tool link and a third wheel fixed to each other and pivotally connected with the fourth pivoting portion of the second bent link; and
    a second flexible rope wound around the second and third wheels and fixed to the first bent link for driving the third wheel and the tool link to rotate about the fourth axis when the second wheel rotates,
    wherein the first and second bent links are substantially equal in length, and wherein an outer radius of the first wheel equals that of the third wheel and doubles that of the second wheel.

2. The robotic arm as claimed in claim 1, wherein the third imaginary axis coincides with the first axis.

3. A robotic arm comprising:
    a first bent link having first and second pivoting portions at two ends thereof respectively and defined with first and second axes passing through the first and second pivoting portions respectively and intersecting at a center of spherical rotation;
    a first driving unit for driving the first bent link to rotate about the first axis;
    a first wheel defined with a third axis passing through the center of spherical rotation;
    a second driving unit for driving the first wheel to rotate about the third axis;
    a second bent link having third and fourth pivoting portions at two ends thereof respectively and defined with a fourth axis passing through the fourth pivoting portion and the center of spherical rotation, the third pivoting portion of the second bent link being pivotally connected with the second pivoting portion of the first bent link;
    a second wheel fixed to the third pivoting portion of the second bent link and pivotally connected with the second pivoting portion of the first bent link;
    a first flexible rope wound around the first and second wheels and fixed to the second bent link for driving the second wheel and the second bent link to rotate about the second axis when the first wheel rotates;
    a tool link and a third wheel fixed to each other and pivotally connected with the fourth pivoting portion of the second bent link; and
    a second flexible rope wound around the second and third wheels and fixed to the first bent link for driving the third wheel and the tool link to rotate about the fourth axis when the second wheel rotates, wherein the first bent link has a tension adjuster and wherein the second flexible rope is fixed to the tension adjuster of the first bent link.

4. A robotic arm comprising:
    a first bent link having first and second pivoting portions at two ends thereof respectively and defined with first and second axes passing through the first and second pivoting portions respectively and intersecting at a center of spherical rotation;
    a first driving unit for driving the first bent link to rotate about the first axis;
    a first wheel defined with a third axis passing through the center of spherical rotation;
    a second driving unit for driving the first wheel to rotate about the third axis;
    a second bent link having third and fourth pivoting portions at two ends thereof respectively and defined with a fourth axis passing through the fourth pivoting portion and the center of spherical rotation, the third pivoting portion of the second bent link being pivotally connected with the second pivoting portion of the first bent link;

a second wheel fixed to the third pivoting portion of the second bent link and pivotally connected with the second pivoting portion of the first bent link;

a first flexible rope wound around the first and second wheels and fixed to the second bent link for driving the second wheel and the second bent link to rotate about the second axis when the first wheel rotates;

a tool link and a third wheel fixed to each other and pivotally connected with the fourth pivoting portion of the second bent link; and a second flexible rope wound around the second and third wheels and fixed to the first bent link for driving the third wheel and the tool link to rotate about the fourth axis when the second wheel rotates, wherein the second bent link has a tension adjuster and wherein the first flexible rope is fixed to the tension adjuster of the second bent link.

5. The robotic arm as claimed in claim 1, wherein the first bent link has two bars moving synchronously; the second bent link and the first and second wheels are located between the bars.

\* \* \* \* \*